United States Patent [19]

Loo

[11] 4,301,002

[45] Nov. 17, 1981

[54] HIGH EFFICIENCY VIRTUAL IMPACTOR

[75] Inventor: Billy W. Loo, Oakland, Calif.

[73] Assignee: The United States of America as represented by the United States Department of Energy, Washington, D.C.

[21] Appl. No.: 134,351

[22] Filed: Mar. 27, 1980

[51] Int. Cl.³ .............................................. B07B 7/086
[52] U.S. Cl. ...................................... 209/143; 73/28
[58] Field of Search ............... 209/143, 145, 1; 73/28, 73/432 PS, 421.5 R; 55/270, 319, 320, 324, 434, 439, 17, 445, 446

[56] References Cited

U.S. PATENT DOCUMENTS

| | | | |
|---|---|---|---|
| 2,932,394 | 4/1960 | McGinn | 209/135 |
| 3,691,735 | 9/1972 | Knierim | 55/391 |
| 3,711,707 | 1/1973 | Lilienfeld et al. | 73/28 X |
| 3,724,658 | 4/1973 | Stephenson | 209/143 |
| 3,731,464 | 5/1973 | Brumbaugh et al. | 209/143 X |
| 3,739,627 | 6/1973 | Klingler | 73/28 |
| 3,771,291 | 11/1973 | Klingler | 55/261 |
| 3,854,321 | 12/1974 | Dahneke | 73/28 |
| 3,859,205 | 1/1975 | Reba et al. | 209/3 |
| 3,883,423 | 5/1975 | Turner et al. | 209/143 |
| 3,901,798 | 8/1975 | Peterson | 209/143 |
| 3,938,366 | 2/1976 | Wertlake et al. | 73/28 |
| 3,954,428 | 5/1976 | Marple et al. | 55/270 |
| 4,023,398 | 5/1977 | French et al. | 73/23 |

FOREIGN PATENT DOCUMENTS 1015882 1/1966 United Kingdom ................. 209/145

OTHER PUBLICATIONS

McFarland et al., "Particle Collection Characteristics of a Single-Stage Dichotomous Sampler", Envir. Sci. & Tech., vol. 12, No. 6, pp. 679-682, Jun. 1978.
Connor, "An Inertial-Type Particle Separator for Collecting Large Samples," J. Air Pollution Control Assn., vol. 16, No. 1, pp. 35-38, Jan. 1966.
Loo et al., Report LBL-8725, "A Second Generation Dichotomous Sampler for Large Scale Monitoring of Airborne Particulate Matter", Apr. 1979.
Loo et al., Report LBL-3854, "Dichotomous Virtual Impactors for Large Scale Monitoring of Airborne Particulate Matter," May 1975.

Primary Examiner—Ralph J. Hill
Attorney, Agent, or Firm—L. E. Carnahan; Roger S. Gaither; Richard G. Besha

[57] ABSTRACT

Environmental monitoring of atmospheric air is facilitated by a single stage virtual impactor (11) for separating an inlet flow ($Q_o$) having particulate contaminants into a coarse particle flow ($Q_1$) and a fine particle flow ($Q_2$) to enable collection of such particles on different filters (19a, 19b) for separate analysis. An inlet particle acceleration nozzle (28) and coarse particle collection probe member (37) having a virtual impaction opening (41) are aligned along a single axis (13) and spaced apart to define a flow separation region (14) at which the fine particle flow ($Q_2$) is drawn radially outward into a chamber (21) while the coarse particle flow ($Q_1$) enters the virtual impaction opening (41). Symmetrical outlet means (47) for the chamber (21) provide flow symmetry at the separation region (14) to assure precise separation of particles about a cutpoint size and to minimize losses by wall impaction and gravitational settling. Impulse defocusing means (42) in the probe member (37) provides uniform coarse particle deposition on the filter (19a) to aid analysis. Particle losses of less than 1% for particles in the 0 to 20 micron range may be realized.

15 Claims, 3 Drawing Figures

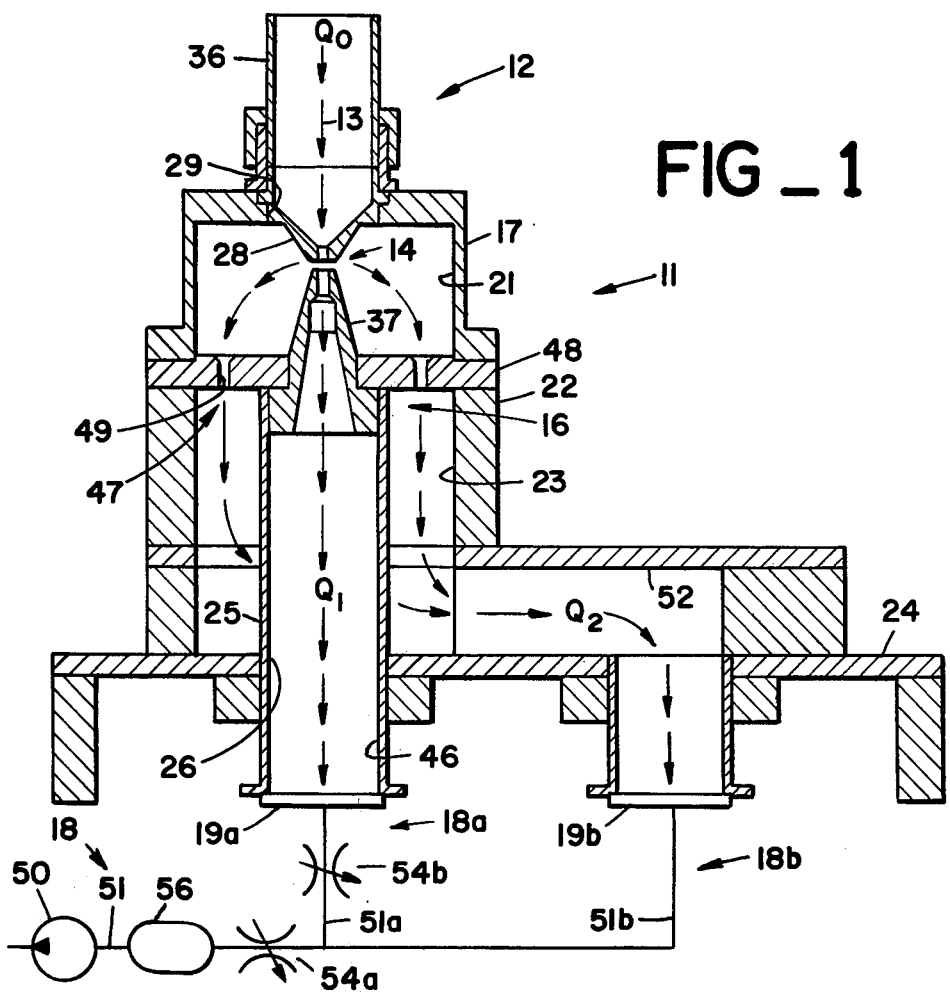
FIG_1
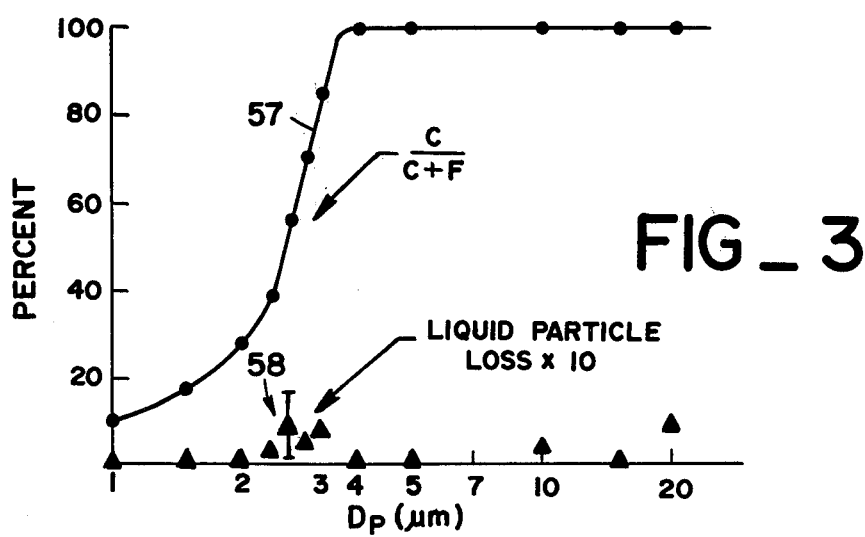
FIG_3

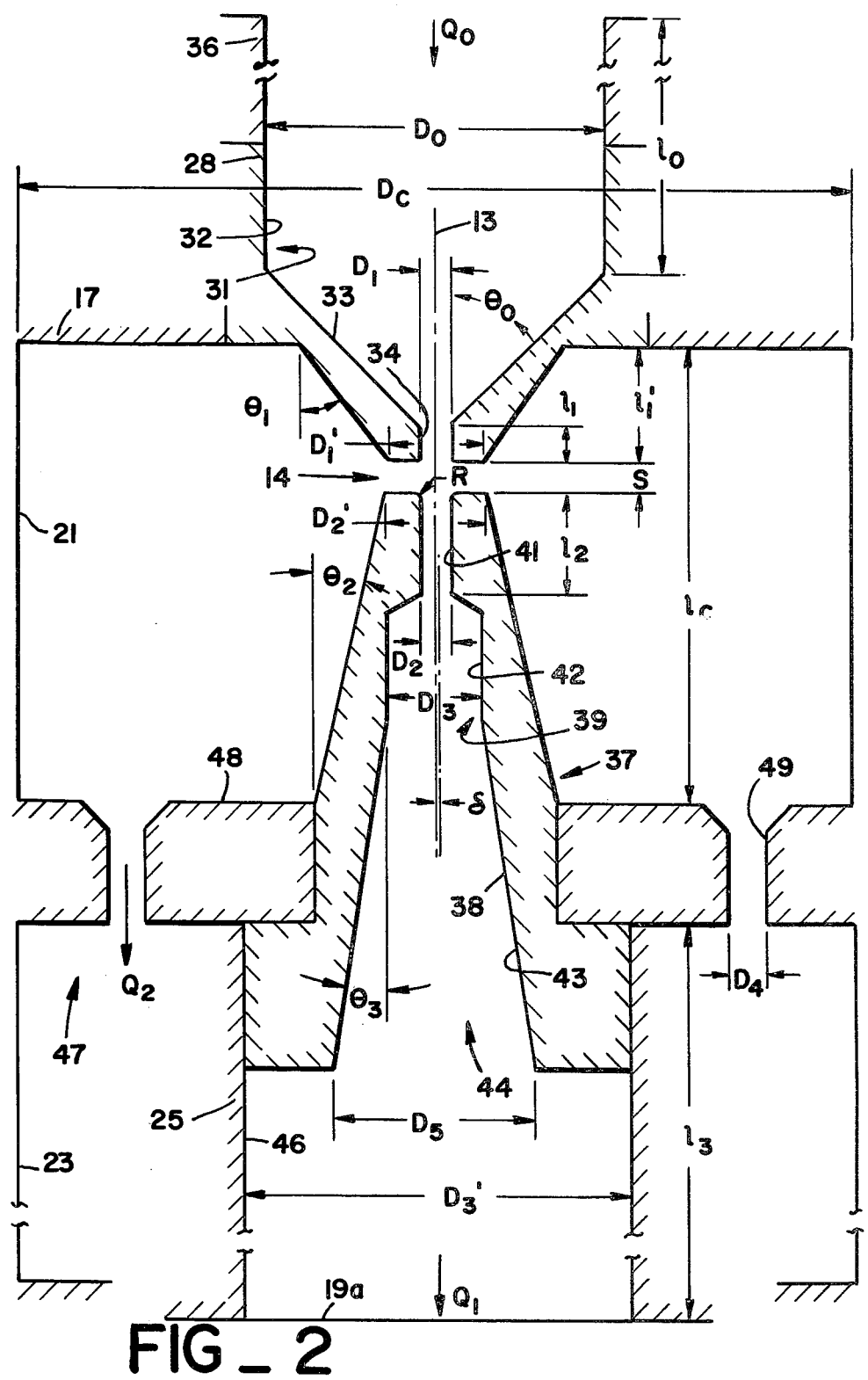
FIG_2

HIGH EFFICIENCY VIRTUAL IMPACTOR

The U.S. Government has rights in this invention pursuant to Contract No. W-7405-eng-48 between the U.S. Department of Energy and the University of California.

BACKGROUND OF THE INVENTION

This invention relates to apparatus for receiving and analyzing particulate matter contained in air or other gases. More particularly the invention relates to virtual impactors for dividing a gas flow into one flow component containing particles larger than a predetermined cutpoint size and another flow component carrying particles of less than the cutpoint size.

Airborne particulate matter variously includes natural aerosals such as soil dust, pollens and sea spray and a large number of other pollutants, such as hydrocarbons, sulphates and nitrates originating from human activities. Particles having aerodynamic sizes below about 15 microns are inhalable by humans and may produce adverse physiological effects. Monitoring of the particulate contaminants of atmospheric air, particularly in urban and industrialized areas, is therefore desirable in order to determine the nature, origin and severity of these effects and to assist in the development of countermeasures and controls.

The inhalable particles present in urban aerosals exhibit a bimodal size distribution having a minimum particle concentration at about 2.5 microns. The fine particle component, having sizes smaller than that value, tends to have a maximum concentration at a size of about 0.3 micron and is primarily derived from combustion products through condensation and coagulation. The coarse particles, having sizes larger than 2.5 microns are primarily of natural origin or are mechanically produced and are typically found in their greatest concentration at sizes around 10 microns.

This bimodal size distribution coincides at least approximately with distinct differences in certain physiological effects of the airborne particles. The fine particles, for example, are much less efficiently removed in the human nasal-pharyngeal regions and therefore penetrate more easily into the tracheo-bronchial and pulmonary regions of the human body.

Thus there are significant differences between the fine and coarse airborne particles with respect to origin, chemical properties, health effects and environmental impact. Accordingly, monitoring and analysis of atmospheric contamination on a continuing basis can be more effective if the fine and coarse particles are separated for separate collection and analysis.

Devices which are commonly used for separating an air sample into first and second flow components, respectively carrying the coarse and fine particles for separate collection and analysis, rely on inertial separation and are referred to as impactors. In one known form, air is drawn by a pump into a particle collection chamber through an inlet flow passage that is directed toward an impaction plate. The particle flow divides at a separation region between the inlet passage and plate with the fine particles being drawn away from the axis of the flow and into the collection chamber while the heavier coarse particles diverge from the axis less strongly and are collected by impaction on the plate. A significant problem with such impactors is that the coarse particles tend to bounce off the impaction plate and become reentrained in the air flow into the fine particle collection region. Deposition of the coarse particles on the impaction plate also tends to be highly nonuniform. This is not compatable with preferred methods of particle analysis such as mass measurement by Beta attenuation and elemental composition determination by x-ray florescence analysis.

These problems have been reduced to some extent by another known type of flow separation device which is commonly referred to as a virtual impactor. In a virtual impactor, the impaction plate is replaced by an annular opening defined by one end of a coarse particle collection probe which receives the coarse particle flow component.

A virtual impactor has several distinct advantages relative to impaction plate devices. Rather than detracting from precision, particle bounce from wall surfaces is a favorable phenomenon in that it reduces losses. As both classes of particles are collected on filters situated a distance away from the flow separation region, sample handling, including automatic sample processing if desired, is facilitated. Particle deposition on collection filters is more uniform and this facilitates x-ray florescence analysis of the collected particles.

As heretofore constructed, virtual impactors do not fully resolve the above discussed problems. Particles with sizes near the cutpoint size tend to impact against structural surfaces around the flow separation region and are effectively lost by adherence to such surfaces or through combining with other impacted particles. Thus prior virtual impactors have tended to exhibit an undesirably high particle loss peak near the cutpoint. Other particles, particularly of the largest sizes, tend to be lost in the inlet flow. The inlet flow progressively increases in velocity as it is decreased in cross-sectional area and the larger, heavier particles resist the necessary changes of trajectory and tend to impact against the wall of the inlet means. Other wall losses occur because of gravitational settling against wall surfaces of the impactor.

To achieve reasonable separation efficiency, prior virtual impactors have required at least two stages of size separation. This aggravates the particle loss problem and such devices typically have a loss peak of about 25 percent at the cutpoint size and of about 60 percent at the large 20 microns size for liquid particles. The complexity and the cost of the instrument are also undesirably large. Further, uniformity of deposition of particles on downstream collection filters has been less than would be desirable for certain method of analysis such as x-ray florescence analysis.

SUMMARY OF THE INVENTION

Accordingly it is an object of the present invention to reduce particle losses within a virtual impactor.

It is another object of this invention to provide a virtual impactor realizing high efficiency and reduced particle loss with a single stage of particle separation.

It is still another object of the invention to provide a virtual impactor, for separating fine particles from coarse particles in a gas flow, which is structurally simple and which may be manufactured at relatively low cost.

It is a further object of the invention to increase the uniformity of deposition of size sorted particles on collection filters in virtual impactors.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, a virtual impactor is provided for dividing a particle containing gas flow into a coarse particle flow component carrying particles of greater than a predetermined cutpoint size and a fine particle flow component carrying particles of less than the cutpoint size. The virtual impactor includes an annular inlet flow tubulation, an annular coarse particle collection probe spaced from the inlet flow tubulation to define a flow separation region, a housing enclosing the flow separation region and defining an annular fine particle flow chamber, the inlet flow tubulation and collection probe and flow chamber being coaxial and aligned along a single axis. First flow producing means withdraw a coarse particle flow component from the separation region through the collection probe, and second flow producing means draw the fine particle flow component outwardly from the separation region and into the flow chamber. The virtual impactor is further provided with the outlet flow path defining means for transmitting the fine particle flow component out of the flow chamber in a flow pattern which is symmetrical with respect to the axis.

In a further aspect of the present invention, in accordance with its objects and purposes, the virtual impactor hereof may also comprise flow acceleration and focusing means for converging a gas flow towards a predetermined linear axis and for directing said converged gas flow along the axis into a flow separation region, first flow component receiving means for receiving a first component of said gas flow which travels across the flow separation region without diverging from travel along the axis by more than a predetermined degree, second flow component receiving chamber means for receiving a second component of the gas flow which diverges from travel along the axis by more than the predetermined degree during flow through the flow separation region, and flow path defining means for causing the second component of the gas flow to travel out of the separation region and away therefrom along a flow path which is symmetrical relative to the axis.

In still a further aspect of the invention, in accordance with its objects and purposes, a virtual impactor for separating particulate matter carried in a gas into a coarse particle flow component and a fine particle flow component, may comprise a coarse particle collecting filter, a coarse particle flow tubulation means for directing the coarse particle flow towards the filter along a flow path having a linear centerline, inlet means for directing the gas towards the tubulation means and which is spaced therefrom to define a flow separation region therebetween, flow producing means for drawing the coarse particle flow component into the tubulation means from the separation region while drawing the fine particle flow component outwardly from the separation region, impulse defocusing means being provided for imparting momentum to the coarse particles that acts to diverge the coarse particles radially outward from the axis during passage of the coarse particles through the tubulation means.

In the preferred forms, the virtual impactor of the present invention requires only a single stage of flow separation while exhibiting extremely sharp particle cut characteristics and very low particle loss and has the further capability of achieving a highly uniform deposition of coarse particles on collection filters to facilitate subsequent analysis. These desirable performance characteristics may be realized with an impactor construction which is structurally simple and therefore capable of being economically manufactured for widespread use in the monitoring of atmospheric contamination.

BRIEF DESCRIPTION OF THE DRAWINGS

The accompanying drawings, which are incorporated in and form a part of the specification, illustrate a preferred embodiment of the invention and, together with the description, serve to explain the principles of the invention. In the drawings:

FIG. 1 is a elevation section view of a virtual impactor embodying the invention, associated components for generating an air flow through the impactor being depicted in schematic form.

FIG. 2 is an enlarged diagrammatic elevation section view of the internal flow regions of the virtual impactor of FIG. 1 with significant configurational parameters being identified in the figure by letter designations to facilitate an understanding of the following description of a preferred embodiment.

FIG. 3 is a graphical depiction of particle size separation efficiency and of wall losses as a function of particles size in the virtual impactor of FIGS. 1 and 2.

DETAILED DESCRIPTION OF THE INVENTION

Reference wil now be made in detail to the present preferred embodiment of the invention, an example of which is illustrated in the accompanying drawings.

Referring initially to FIG. 1, the virtual impactor 11 of this example includes inlet flow tubulation 12 which functions as flow acceleration and focusing means for converging an inlet gas flow $Q_0$ towards a predetermined linear axis 13 defined by the centerline of the tubulation and for directing the converged gas flow along the axis to a flow separation region 14. The virtual impactor 11 further includes coarse particle flow tubulation or receiving means 16 which functions as a collection probe for receiving the portion $Q_1$ of the inlet gas flow $Q_0$ that travels across the separation region 14 without diverging from the axis 13 by more than a predetermined degree. A housing 17 defines a second or fine particle flow component receiving chamber means for receiving the portion $Q_2$ of the inlet gas flow $Q_0$ that diverges from the axis 13 by more than the predetermined degree during travel through the flow separation region 14. First and second flow producing means, 18a and 18b respectively, are provided for drawing the gas flow $Q_0$, such as atmospheric air containing particulate matter, into the inlet flow tubulation 12 and for drawing the first or coarse particle flow component $Q_1$ into coarse particle flow tubulation 16 while also drawing the second or fine particle flow component $Q_2$ outwardly at separation region 14 and into the second flow component receiving means 17. The flow producing means 18a, and 18b draw flow component $Q_1$ through a coarse particle collection filter 19a while drawing flow component $Q_2$ from fine particle flow chamber 21 through a separate fine particle collection filter 19b.

Considering a suitable structure for the virtual impactor 11 in more detail, an upright cylindrical fine particle flow component receiving tube 22 having an internal flow passage 23 is secured to a base platform, 24, the centerline of the tube being coincident with axis 13. A cylindrical coarse particle flow receiving tube 25 extends upwardly through an opening 26 in base platform 24 and along axis 13 within the fine particle flow receiving tube 22. Thus tubes 25 and 22 are coaxial and share a single centerline defined by axis 13.

Housing 17 which defines the cylindrical fine particle flow chamber 21 is supported on the upper end of fine particle flow receiving tube 22 in coaxial relationship with the tube.

The inlet flow acceleration and focusing means tubulation 12 of this example includes a flow acceleration nozzle 28 secured to housing 17 and which extends through an opening 29 in the housing to flow separation region 14. Referring to FIG. 2 which depicts the structure on a larger scale, the annular inner wall 31 of nozzle 28 has an uppermost inlet flow passage portion 32 of uniform diameter, an intermediate flow accelerating and focusing portion 33 which progressively decreases in diameter in the downward direction and a lowermost jet orifice portion 34 having a uniform diameter $D_1$ smaller than the diameter $D_0$ of the uppermost portion 32.

Referring again to FIG. 1, an inlet tube 36, extends upward from nozzle 28, in alignment with flow axis 13, and has an inner diameter similar to that of the uppermost portion of nozzle.

The coarse particle flow tubulation 16 of this example includes an annular collection probe member 37 secured, in coaxial relationship, to the upper end of coarse particle receiving tube 25 and which extends upward into housing 17. The upper end of collection probe member 37 is spaced apart from the lower end of nozzle 28 to define the flow separation region 14.

Referring again to FIG. 2, collection probe member 37 has an annular inner wall 38 defining an internal coarse particle flow passage 39 from the flow separation region 14 to coarse particle receiving tube 25, the passage being symmetrical with respect to axis 13. A first portion of passage 39 constitutes a coarse particle receiving virtual impaction opening 41 which is adjacent to flow separation region 14 and which is of greater diameter than the jet orifice portion 34 of the nozzle 28.

In addition to the transmitting of coarse particles to collection filter 19a, the lower portions or sections 42 and 43 of the probe member flow passage 39 constitute impulse defocusing means 44 for imparting momentum to the coarse particles which acts to diverge the particles outwardly from axis 13 to increase uniformity of deposition of the particles on the filter. A first impulse defocusing portion 42 of passage 39, immediately below virtual impaction opening 41, provides an abrupt increase in the diameter of the passage. Radial expansion of the flow $Q_1$ as it enters passage portion 42 imparts the radially outward momentum to the particles. The next portion 43 of passage 39 is a defocusing section of progressively increasing diameter in the flow direction and provides for a radial expansion of the coarse particle flow in response to the radial momentum. The diameter of passage portion 43 increases in the direction of flow $Q_1$ from a diameter corresponding to that of portion 42 to a larger diameter which is slightly smaller than that of the internal flow passage 46 of the coarse particle receiving tube 25.

Referring again to FIG. 1, realization of a desirably sharp division between the coarse particle flow $Q_1$ and the fine particle flow $Q_2$ with minimized particle losses from impaction against wall surfaces requires strict flow pattern symmetry, relative to axis 13, within the separation region 14. The symmetrical configurations and coaxial realtionship of the annular inner surfaces of inlet flow tubulation 12, collection probe member 37 and housing 17 contribute to this objective but in the absence of further novel structure do not assure that such flow pattern symmetry is achieved to the most desirable extent. If the fine particle flow component $Q_2$ is transmitted out of chamber 21 along a flow path which is asymetrical relative to axis 13, as has been the practice in prior constructions, the outward flow pattern of flow $Q_2$ at separation region 14 is affected in such a manner that the focus of the particles emanating from nozzle 28 is distorted and wall losses are significantly increased. Adverse effects from asymmetry of the outward flow $Q_2$ at separation region 14 are avoided in the present invention by outlet flow path defining means 47 for transmitting the fine particle flow component $Q_2$ out of flow chamber 21 in a flow pattern which is symmetrical with respect to the axis 13. This causes the fine particle flow $Q_2$ to travel radially outwardly from axis 13 at the flow region 14 in a flow pattern in which the flow velocity and volume is identical in all radial directions.

The outlet flow path defining means 47 in this example includes a plate member 48 forming a circular apertured endwall of chamber 21 through which the fine particle flow $Q_2$ is transmitted to fine particle receiving tube 22. Plate member 48 is coaxially positioned relative to flow tubulations 12 and 16 and has a plurality of flow apertures 49 through which chamber 21 is communicated with the upper end of receiving tube 22. Apertures 49, of which there are eight in this embodiment are located in plate member 48 to be equidistant from axis 13 and to be equiangularly spaced around the axis. To assure an outlet flow path from chamber 21 that is symmetrical with respect to axis 13, each aperture 49 must be small enough to produce a sizable flow impedance while being large enough to avoid particle losses.

The flow producing means 18 in this example includes a pump 50 having a branched inlet conduit 51 with a first branch 51*a* being communicated with the lower end of coarse particle receiving tube 25 through coarse particle collection filter 19*a* and having a second branch 51*b* communicated with the lower end of fine particle receiving tube 22 through fine particle collection filter 19*b* and a flow conduit 52 which extends outwardly and then downwardly from the lower end of fine particle receiving tube 22. To enable adjustment of the magnitudes of flows $Q_1$ and $Q_2$, a first variable orifice valve 54*a* is connected into the pump inlet line 51 and a second variable orifice valve 54*b* is situated in branch line 51*a* and may be controlled by automatic means of known form if desired. To dampen pressure variations which may be generated by the pump 49, an accumulator or surge chamber 56 is provided in the pump inlet line 51.

The performance of the virtual impactor 11 with respect to achieving precise separation of particles about the cutpoint, with respect to minimizing particle loss and with respect to realizing uniformity of deposition of the coarse particles on collection filter 19*a* is sensitive to a number of flow parameters and configurational parameters which are identified in FIG. 2 by letter symbols. Specific values and ranges of values which are given in the following discussion of such parameters should be understood to be examples applying to the herein described preferred embodiment and do not necessarily apply to all embodiments or variations of the invention.

For the reasons previously discussed, the cutpoint particle size in this example is selected to be 2.5 microns, that is the coarse particle flow component $Q_1$ is to receive particles having an aerodynamic size (Stokes diameter) greater than 2.5 microns while the fine particle flow component $Q_2$ carries particles of smaller size. The inlet flow $Q_0$ in this example is about one cubic meter of air per hour. The inlet flow velocity $Q_0$ within inlet tube 36 is selected to minimize losses the the heavier coarse particles. A high inlet flow velocity increases coarse particle loss by impaction against wall surfaces as intertial effects cause such heavy particles to resist the trajectory changes needed to focus the inlet flow towards axis 13. Conversely, a low inlet flow velocity increases coarse particle loss by gravitational settling onto the interior wall of the inlet tube as this form of loss is a function of the time which particles spend in the flow. Given the particle size range of interest in this example, specifically particles having sizes up to 20 microns, such losses are minimized by establishing an inlet velocity in the range from about 35 cm/sec to about 53 cm/sec, an inlet velocity of 43.4 cm/sec being preferred.

Determination of the inlet flow velocity enables optimization of other sensitive parameters. To enable realization of the desired cutpoint, the coarse particle flow component $Q_1$ is fixed to be in the range of from about 5% to about 10% of $Q_0$, a $Q_1/Q_0$ ratio of 0.1 being utilized in this example. Selection of the inlet flow $Q_0$ and the $Q_1/Q_0$ ratio for these purposes may be accomplished by adjusting pump 50 and valves **54*a* and 54*b* of FIG. 1**.

Referring again to FIG. 2, the diameter $D_1$, of jet orifice 34 determines flow velocity into separation region 14 and is a major factor in establishing the cutpoint, $D_1$ being 0.305 cm in the present embodiment. Diameter $D_2$ of virtual impaction opening 41 is fixed to cause the ratio $D_2/D_1$ to be in the range from about 1.3 to about 1.4 to minimize wall losses, in the separation region, of particles having sizes near the cutpoint size. A $D_2/D_1$ ratio of 1.38 is used in this particular embodiment and thus $D_2$ is 0.422 cm in this example.

Flow symmetry and particle loss are highly sensitive to the degree of alignment of the centerlines of nozzle 28 and collection probe member 37 but as a practical matter some misalignment is likely to occur from manufacturing imprecision or other causes. To realize the preferred performance characteristics of this example of the invention, the misalignment displacement $\delta$ should not exceed 0.005 cm.

The spacing, S, between nozzle 28 and probe member 37 is preferrably fixed as a proportion of $D_1$ and in the present example an $S/D_1$ ratio of 1.04 minimizes particle loass from impaction against the end of the collection probe. Thus S is 0.318 cm in this example.

Other configurational parameters which affect particle losses include the outer diameter $D_1'$, of the lower end of nozzle 28 which is sized to minimize back impaction losses from contact of particles on the end of the nozzle. Given the other parameters of this particular embodiment, $D_1'$ is preferrably about 0.714 cm. To direct particles into the flow separation region 14 along trajectories which are sufficiently parallel to flow axis 13, the length $l_1$ of the lower portion 34 of nozzle 28 in this example is made equal to 1.04 $D_1$ and is therefore 0.318 cm. Nozzle 28 extends into chamber 23 a distance $l_1'$ sufficient to minimize back impaction losses against the upper inner wall of housing 22, this distance having been found to be 0.952 cm in the present embodiment.

The radius, R, of the rounded shoulder of impaction opening 41 of probe member 37 is selected to be large enough to provide for a smooth return to the $Q_2$ flow streamlines of fine particles which may penetrate slightly into impaction opening 41 of the collection probe 37 while being small enough to avoid perturbation of the flow geometry in the separation region 14 and in the present example has been optimized at a value of 0.089 cm. Selection of the inner diameter of $D_c$ of chamber 23 is also a matter of balancing opposing considerations. $D_c$ should be large enough to avoid losses by particle impaction against the inner wall of housing 22 while being small enough to minimize gravitational settling of particles, the optimized value for $D_c$ in this embodiment being 7.62 cm. Impaction losses agains the inner wall of coarse particle receiving tube 25 are minimized by making the inside diameter $D_3'$ of tube 25 at least as large as that of the filter **19*a***, $D_3'$ being 3.175 cm in this example.

An angle, $\theta_0$, of about 45° relative to axis 13 has been found to be optimum for the focusing and acceleration portion 33 of the nozzle 28 passage in order to minimize wall loss of particles. The diameter, $D_0$ of the upper inlet portion 32 of the flow passage through nozzle 28 is large enough to admit the coarser particles into the nozzle without impaction loss while being small enough to minimize gravitational settling losses and in the present example an inlet diameter of 2,858 cm has been found to be optimum. The total length $l_0$ of the inlet tube 36 together with the uppermost inlet portion 32 of the nozzle 28 is made long enough to establish a symmetrical aerosol distribution in the inlet passage. In the present example a length $l_0$ of 30 cm to 60 cm has been found to be sufficient.

The depth, $l_c$ of chamber 23 should be sufficient to prevent impaction of fine particles on support plate 24, a depth $l_c$ of 4.44 cm being sufficient for this purpose in the present example. The apertures 49 are sized to provide sufficient impedence to flow $Q_2$ to assure azimuthal flow symmetry in the separation region 14 and have a diameter of 0.318 cm in the present embodiment.

Further significant parameters of the coarse particle collection probe member 37 include the outside diameter $D_2'$ of the upper end of the probe which should be small enough in relation to the inside diameter $D_2$ to enable prompt defocusing or vertical spreading of the fine particle flow $Q_2$ as it leaves the separation region 14, $D_2'$ being 0.635 cm in the present embodiment. The diameter $D_3$ of the intermediate portion 42 of passage 39 of probe member 37 is made sufficiently greater than the diameter $D_2$ of the virtual impaction opening to cause an impulse defocusing or radial spreading of the coarse particle flow $Q_1$ and in this embodiment is 0.952 cm. The lower portion 43 of the internal passage 39 of probe member 37 expands in the downward direction at an angle $\theta_3$ of 7° in this embodiment which provides for subsequent radial spreading of the coarse particles in flow $Q_1$ across the full area of the coarse particle receiving tube 24. The length $l_2$ of virtual impaction opening 41 of probe member 37 is 0.793 cm in this example which length is sufficiently small to avoid over-concentration of the coarse particle flow at the center region of filter **19*a* while being large enough to extend the region of inertial separation slightly into the uppermost portion of probe member 37**.

To reduce back impaction losses against the outer surface of nozzle 28 within chamber 23, the portion of the nozzle which extends within the chamber is conical and forms an angle $\theta_1$ of 30° in this embodiment with respect to the flow axis 13. The portion of probe member 37 which extends into chamber 23 is also conical to promote defocusing or vertical spreading of the fine particle flow $Q_2$ as it leaves the separation region 14 and in this embodiment forms an angle $\theta_2$ of 15° relative to the flow axis 13.

The length $l_3$ of the coarse particle receiving tube 24 is sufficient to provide for uniform distribution of the coarse particles on filter 19 following the impulse defocusing initiated by the probe member 37 configuration and in this embodiment is 11.43 cm.

It should be understood that departures from the above described specific parameters are possible in other embodiments, the specific values given above for purposes of example having been empirically determined to be optimum for the specific virtual impactor 11 which has been herein described. Many of the above described sensitive parameters are interrelated and changes in one may require changes in others in order to continue to realize optimized performance of the virtual impactor.

In operation, the virtual impactor 11 is typically employed for monitoring particulate contamination in atmospheric air. At the start of a sampling period, clean filters 19a and 19b are installed and pump 50 is operated to draw air from both coarse particle receiving tube 25 and fine particle receiving tube 22 through the filters 19a and 19b respectively. The desired inlet flow velocity for flow $Q_0$ and the desired proportionate division of inlet flow $Q_0$ between coarse particle flow $Q_1$ and fine particle flow $Q_2$, in accordance with the parameters as hereinbefore described, is established by adjustment of the pump 50 and variable orifice valves 54a and 54b. As inlet flow rate is known, the volume of air processed during a given sampling may be determined by multiplying the inlet flow rate by the sampling time.

The inlet flow is converged or focused towards axis 13 in nozzle 28 and consequently to flow velocity increase occurs. Particles which are carried in the flow acquire additional momentum which causes the particles to exhibit an increasing inertial resistance to changes of flow trajectory. At the flow separation region 14 the momentum prevents the larger, heavier particles from diverging from axis 13 sufficiently to enter the outward fine particle flow $Q_2$ although the fine particles which have less inertial resistance to trajectory change are able to do so.

Accordingly, the coarse particles enter impaction opening 41 and are carried to filter 19a where such particles are collected for subsequent analysis. The abrupt expansion of the coarse particle flow path between impaction opening 41 and portion 42 of the internal passage of probe member 37 imparts radial momentum to the coarse particles in flow $Q_1$. This causes such particles to diverge radially from axis 13 during subsequent travel towards filter 19a and provides for uniformity of deposition of the particles on the filter.

The fine particles are carried radially outwardly from axis 13 at separation region 14 by the radially directed fine particle flow $Q_2$ and are subsequently collected by filter 19b. Symmetry of the flow pattern at the separation region 14 is assured by the outlet flow path means 47 from chamber 47 which, by being symmetrical with respect to axis 13, assures that the velocity and volume of the radially outward flow at region 14 is the same in all radial directions relative to axis 13.

Following a period of operation, filters 19a and 19b are removed for separate analysis of the collected coarse and fine particles by known techniques, x-ray florescence analysis being a preferred procedure.

Referring to FIG. 3, curve 57 depicts measured size separation characteristics as a function of particle size in a virtual impactor having the previously described configurational and operational parameters. More specifically, curve 57 depicts variation of the factor C/(C+F) with particle size where C and F represent particle collections on the coarse and fine particle collecting filters 19a and 19b respectively. Points 58 of FIG. 3 depict measured wall losses as a function of particle size, the percentage loss as shown in FIG. 3 being ten times greater than the actual measured loss in order to give the points 58 a discernable value in the scale of the drawing. As may be seen from points 58, no significant losses occur at sizes below the cutpoint. The maximum loss peak near the cutpoint is slightly under 1% as measured although some measurement uncertainty is present as indicated by the error bar. Losses begin to rise above a negligible level at the upper end of the size range, the measured loss of 20 micron sized particles being about 1%.

The foregoing description of a preferred embodiment of the invention has been presented for purposes of illustration and description. It is not intended to be exhaustive or to limit the invention to the precise form disclosed, and obviously modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A virtual impactor for dividing a particle containing gas flow into a coarse particle flow component carrying particles larger than a predetermined cutpoint size and a fine particle flow component carrying particles of less than said cutpoint size, said virtual impactor having an annular inlet flow tubulation, an annular coarse particle collection probe spaced from said inlet flow tubulation to define a flow separation region therebetween, a housing enclosing said separation region and defining an annular fine particle flow chamber therearound, said inlet flow tubulation and said collection probe and flow chamber being coaxial and aligned along a single linear axis, a coarse particle collector disposed within said probe in symmetrical relationship to said axis, a fine particle collector disposed outside of said flow chamber and at a position offset from said axis, first flow producing means for drawing said coarse particle flow component from said separation region into said collection probe and to said coarse particle collector therein, flow passage means for receiving said fine particle flow from said flow chamber and for transmitting said fine particle flow outwardly away from said axis to said fine particle collector, and second flow producing means for drawing said fine particle flow component outwardly from said separation region into said flow chamber and then to said fine particle collector through said flow passage means, wherein the improvement comprises:

a flow chamber endwall disposed between said flow chamber and said flow passage means in coaxial relationship to said inlet flow tubulation and said probe, said endwall having aperture means for transmitting said fine particle flow component out of said flow chamber and into said flow passage means in a flow pattern which is symmetrical with respect to said axis, said aperture means being sized to impede flow from said chamber into said flow passage means to an extent sufficient to prevent flow pattern asymmetry in said flow passage means from causing a flow pattern asymmetry at said separation region.

2. A virtual impactor as set forth in claim 1 wherein said collection probe has an annular coarse particle flow passage with an end adjacent said separation region that defines a virtual impaction opening, said end of said coarse particle flow passage being of progressively increasing diameter towards said separation region to cause said virtual impaction opening to have a rounded profile adjacent said separation region.

3. A virtual impactor as set forth in claim 1 wherein said aperture means includes a plurality of flow apertures through said endwall through which said fine particle flow component is withdrawn from said flow chamber, said flow apertures being equidistant from said axis and being equiangularly spaced apart around said axis and collectively having an area sufficiently small to establish said flow impedance.

4. A virtual impactor as set forth in claim 1 whrein said flow passage means includes a fine particle flow component receiving tube disposed adjacent said outlet flow path defining means and having an internal flow passage which receives said fine particle flow component therefrom, at least the portion of said internal passage which is adjacent said outlet means being annular and being coaxial with said inlet flow tubulation and said probe and said flow chamber and further includes a flow conduit extending radially from said internal flow passage to said fine particle collector.

5. A virtual impactor for dividing a particle containing gas flow into a coarse particle flow component carrying particles larger than a predetermined cutpoint size and a fine particle flow component carrying particles of less than said cutpoint size, said virtual impactor having an annular inlet flow tubulation, an annular coarse particle collection probe spaced from said inlet flow tubulation to define a flow separation region therebetween, a housing enclosing said separation region and defining an annular fine particle flow chamber therearound, said inlet fow tubulation and said collection probe and flow chamber being coaxial and aligned along a single linear axis, first flow producing means for withdrawing said coarse particle flow component from said separation region through said collection probe, and second flow producing means for drawing said fine particle flow component outwardly from said separation region and into said flow chamber, wherein the improvement comprises:

outlet flow path defining means for transmitting said fine particle flow component out of said flow chamber in a flow pattern which is symmetrical with respect to said axis, and wherein said inlet flow tubulation forms an inlet flow passage having a jet opening adjacent said separation region and having a flow acceleration and focusing portion of progressively decreasing diameter which directs said gas flow to said jet opening, and wherein said collection probe forms a coarse particle flow passage having a virtual impaction opening adjacent said separation region and a flow defocusing portion including a first impulse defocusing section which is of abruptly increased diameter and a subsequent section which increases in diameter more gradually.

6. A virtual impactor as set forth in claim 5 further comprising a coarse particle flow receiving tube disposed in coaxial relationship with said collection probe and having an annular internal passage which communicates with said coarse particle receiving passage of said collection probe and which has a greater diameter than said subsequent section of said coarse particle receiving passage.

7. A virtual impactor as set forth in claim 5 wherein the ratio of the inner diameter of said collection probe at said separation region to the inner diameter of said inlet flow tubulation at said separation region is in the range from about 1.3 to about 1.4 and wherein said first flow producing means draws from about 5% to about 10% of said gas flow into said collection probe.

8. A virtual impactor as set forth in claim 7 wherein said cutpoint particle size is about 2.5 microns and flow regulating means for maintaining said gas flow into said inlet flow tubulation at a mean velocity in the range from about 35 cm/sec to about 53 cm/sec.

9. A virtual impactor comprising:

flow acceleration and focusing means for converging a gas flow and particles carried thereby towards a predetermined linear axis and for directing said converged gas flow along said axis into a flow separation region, first flow component receiving means for receiving a first component of said gas flow and said particles which travels across said flow separation region without diverging from travel along said axis by more than a predetermined degree, said first flow component receiving means having a flow passage through which said first flow component travels away from said separation region, said flow passage being defined by an annular inner wall surface which is symmetrical with respect to said axis, impulse defocusing means for imparting momentum to particles carried by said first flow component that acts to diverge said particles outwardly from said axis within said first flow component receiving means, said impulse defocusing means including first, second and third portions of said annular inner wall surface which are progressively further from said separation region, said second portion being of abruptly increased diameter relative to said first portion and said third portion being of greater diameter than said second portion, second flow component receiving chamber means for receiving a second component of said gas flow which diverges from travel along said axis by more than said predetermined degree during flow through said flow separation region, and flow path defining means for causing said second component of said flow to travel out of said separation region and away therefrom along a flow path which is symmetrical relative to said axis.

10. A virtual impactor as defined in claim 9 wherein said flow path defining means comprises a tubulation disposed symmetrically with respect to said axis and having an annular internal passage positioned to receive said second flow component from said chamber means and to transmit said second flow component away therefrom along a flow path extending parallel to said axis.

11. A virtual impactor as defined in claim 10 wherein said flow path defining means further comprises a plate member disposed in the flow path between said chamber means and said tubulation and having at least one aperture for transmitting said second flow component therebetween in said symmetrical flow path.

12. A virtual impactor comprising:
flow acceleration and focusing means for converging a gas flow towards a predetermined linear axis and for directing said converged gas flow along said axis into a flow separation region,
first flow component receiving means for receiving a first component of said gas flow which travels across said flow separation region without diverging from travel along said axis by more than a predetermined degree, said first flow component receiving means having an annular internal flow passage for transmitting said first flow component including particles entrained therein away from said separation region and further including impulse defocusing means for imparting momentum to said particles which acts to diverge said particles from said axis as said particles travel along said internal flow passage, wherein said impulse defocusing means includes an annular inner wall surface of said first flow component receiving means having one portion of progressively increasing diameter in the direction of flow therethrough and having another portion situated between said one portion and said separation region and which increases in diameter more abruptly, second flow component receiving chamber means for receiving a second component of said gas flow which diverges from travel along said axis by more than said predetermined degree during flow through said flow separation region, and
flow path defining means for causing said second component of said flow to travel out of said separation region and away therefrom along a flow path which is symmetrical relative to said axis.

13. In a virtual impactor for separating particulate matter carried in a gas into a coarse particle flow component and a fine particle flow component, the virtual impactor having a coarse particle collecting filter, a coarse particle flow tubulation means for directing said coarse particle flow towards said filter along a flow path having a linear centerline and which is bounded by an aannular inner wall surface of said tubulation means, inlet means for directing said gas towards said tubulation means and which is spaced therefrom to define a flow separation region therebetween, flow producing means for drawing said coarse particle flow component into said tubulation means from said separation region while drawing said fine particle flow component outwardly from said separation region, wherein the improvement comprises:
impulse defocusing means for imparting momentum to said coarse particles that acts to diverge said coarse particles radially outward from said axis during passage of said coarse particles through said tubulation means, said impulse defocusing means including first, second and third portions of said annular inner wall surface which are successively further from said separation region, aid second portion being of abruptly increased diameter relative to said first portion, and said third portion being of greater diameter than said second portion.

14. In a virtual impactor for separating particulate matter carried in a gas into a coarse particle flow component and a fine particle flow component, the virtual impactor having a coarse particle collecting filter, a coarse particle flow tubulation means for directing said coarse particle flow towards said filter along a flow path having a linear centerline, inlet means for directing said gas towards said tubulation means and which is spaced therefrom to define a flow separation region therebetween, flow producing means for drawing said coarse particle flow component into said tubulation means from said separation region while drawing said fine particle flow component outwardly from said separation region, wherein the improvement comprises:
impulse defocusing means for imparting momentum to said coarse particles that acts to diverge said coarse particles radially outward from said axis during passage of said coarse particles through said tubulation means, wherein said impulse defocusing means includes an annular inner wall of said tubulation means that defines at least a portion of said flow path, said annular inner wall having one section of progressively increasing diameter in the flow direction and having a preceding section which increases in diameter more abruptly.

15. The apparatus of claim 14 wherein said annular inner wall of said tubulation means has still another section situated between said one section and said filter and which has a diameter larger than the largest diameter of said one section.

* * * * *